United States Patent [19]

Giller et al.

[11] 4,039,546
[45] Aug. 2, 1977

[54] METHOD OF PREPARING $N_1$-(2'-FURANIDYL)-5-SUBSTITUTED URACILS

[76] Inventors: Solomon Aronovich Giller, ulitsa Pernavas, 10, kv. 76, Riga; Arvid Avgustovich Lazdinsh, ulitsa Mendeleeva, 1, kv. 31, Rizhsky raion, Olaine; Artur Karlovich Veinberg, ulitsa Ludzas, 2, Rizhsky raion, Jurmala; Alexandr Borisovich Sidorov, ulitsa Marupes, 12-a, kv. 1, Riga, all of U.S.S.R.

[21] Appl. No.: 572,064

[22] Filed: Apr. 28, 1975

[51] Int. Cl.² ........................................... C07D 239/54
[52] U.S. Cl. ................................................... 260/260
[58] Field of Search ......................................... 260/260

[56] References Cited
U.S. PATENT DOCUMENTS 3,912,734  10/1975  Giller et al. ........................ 260/260

*Primary Examiner*—Paul M. Coughlan, Jr.
*Attorney, Agent, or Firm*—Robert E. Burns; Emmanuel J. Lobato; Bruce L. Adams

[57] ABSTRACT

A method of preparing $N_1$-(2'-furanidyl)-substituted uracils having the general formula

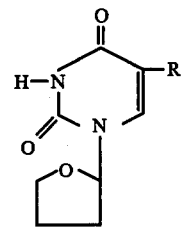

where R is selected from the group consisting of hydrogen, halogen, and alkyl, consists in that 2,3-dihydrofuran is processed with anhydrous hydrogen chloride in a medium of an organic chlorinated aliphatic hydrocarbon solvent, and the thus formed product is reacted with 2,4-bis-(trimethylsilyloxy)-5R-substituted pyrimidines at a temperature not above 10° C with subsequent isolation of the end product.

3 Claims, No Drawings

METHOD OF PREPARING N₁-(2'-FURANIDYL)-5-SUBSTITUTED URACILS

The present invention relates to a method of preparing N₁-(2'-furanidyl)-5-substituted uracils having the general formula

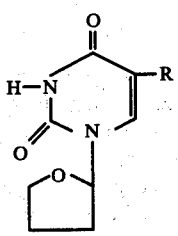

where R is hydrogen, a halogen, or an alkyl.

Said compounds have pharmacological activity; they are antimetabolites of nucleic acid metabolism, and are therefore used in medicine. One of the representatives of said compounds, N₁-(2'-furanidyl)-5-fluorouracil, is an active principle of an antitumour preparation.

Known to the prior art is the method for preparing N₁-(2'-furanidyl)-5R-subsituted uracils consisting in condensation of the corresponding 2,4-bis(trimethyl-silyloxy)-5R-substituted pyrimidines with 2-chlorofuranidine at a temperature of −10° to −20° C. Ethyl alcohol is added to the reaction mixture the precipitate is separated and re-crystallized from water. The yield of the end product, N₁-(2'-furanidyl)-5-fluorouracil, is 66 percent by weight. (See Inventors' Certificate of the USSR No. 287,952).

The disadvantage of the known method is the low yield of the end product, and complexity of the process equipment, which are due to partial polymerization, splitting, and instability of the starting substances.

The object of the invention is to simplify the process equipment and to increase the yield of the end product.

Said object has been accomplished by a method for preparing N₁-(2'-furanidyl)-5-substituted uracils having the general formula

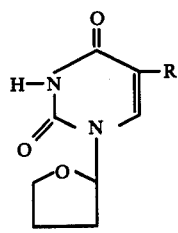

where R is a hydrogen atom, or a halogen, or an alkyl, wherein according to the invention, 2,3-dihydrofuran is treated with dry hydrogen chloride in a medium of an organic chlorinated aliphatic hydrocarbon solvent, and the resultant product is reacted with 2,4-bis-(trimethyl-silyloxy)-5R-substituted pyrimidines at a temperature not above 10° C with subsequent isolation of the end product. (R is as indicated above).

It is recommended that dichloromethane, chloroform, or dichloroethane should be used as the organic chlorinated aliphatic hydrocarbon solvent. The process should be carried out preferably at a temperature of from −5° C to +5° C.

The proposed method can be carried out as follows.

Anhydrous hydrogen chloride is passed through a solution of 2,3-dihydrofuran in the medium of the solvent, preferably dichloromethane, chloroform or dichloroethane, and 2,4-bis (trimethyl silyloxy)-5R-substituted pyrimidine is added. The latter can be added during the passage of the hydrogen chlorine into 2,3-dihydrofuran solution, or after all hydrogen chloride has been passed into the solution. The preferable temperature conditions are from −5° to +5° C. Next ethyl alcohol is added to remove the remaining trimethylsilyl group. The end product is thus precipitated and separated by filtration. The filtrate is evaporated and any residual quantities of the end product are recovered. The yield is 70–80 percent by weight of theory, based upon the starting 5R-substituted uracil.

The proposed method increases the yield of the end product to 80 percent by weight, as against the former 66 percent, simplifies the procedures and equipment, since unstable raw materials are not used strong cooling of the reaction mixture is no longer required. Moreover, the proposed method ensures high quality of the end product (the assay to 90–95 percent), which facilitates its purification and increases the yield of pure product.

For a better understanding of the invention, the following examples of its practical embodiment are given by way of illustration.

EXAMPLE 1

A solution of 175 g of 90 percent 2,3-dihydrofuran (2.25 mole) in 400 ml of dichloromethane is processed at a temperature from −5° to 0° C with 60.0 litres of dry hydrogen chloride by bubbling through the latter at a rate of 150 litres per hour subsequently 2,4-bis(trimethylsilyloxy)-5-fluoropyrimidine is added. The solution of the above ingredients is maintained or 30 minutes at the stated temperature.

The 2,4-bis(trimethylsilyloxy)-5-fluoropyrimidine is prepared by heating to 140° C 217.5 g (1.67 mole) of 5-fluorouracil, 322.0 g (2.0 mole) of hexamethyldisiloxane and 13.8 ml of trimethylchlorosilane until the solid phase 5-fluorouracil disappears.

The yield of 2,4-bis(trimethylsilyloxy)-5-fluoropyrimidine is 485.0 g (assaying 85 percent). This is 90 percent by weight of theory, calculating with reference to the starting 5-fluorouracil.

After keeping said reaction mixture at temperatures for thirty minutes 710 ml of ethyl alcohol are added. The N₁-(2'-furanidyl)-5-fluorouracil precipitates as a white substance. The precipitate is separated by filtration and 270 g of the product are obtained. The filtrate is evaporated and another 36 g of the product are recovered.

The product is re-crystallized from chloroform to obtain 268 g of pure end product (80 percent of theory, calculating with reference to the starting 5-fluorouracil). The m.p. 165° − 167° C.

Found, in percent by weight: C 48.10, H 5.64 N 14.10 $C_8H_9O_3N_2F$ Calculated, in percent by weiight: C 47.99, H 4.50, N 14.00.

EXAMPLE 2

By a procedure similar to that described in Example 1 N₁-(2'-furanidyl)-5-bromouracil is prepared from 5-bromouracil, hexamethyldisiloxane, trimethylchlorosilane, HCl and 2,3 dihydrofuran. Dichloroethane is used as the solvent, and the product is recrystallized from a mixture of ethyl alcohol and water. The yield of the end product is 75 percent of theory calculating with reference to the starting 5-bromouracil. The m.p. 204°-207° C. Found, in percent by weight: C 37.50, H 3.40 N 10.80 Calculated, in percent by weight: C 36.80 H 3.47, N 10,73 $C_8H_9O_3N_2Br$.

EXAMPLE 3

By a procedure similar to described in Example 1, $N_1$-(2'-furanidyl)-5-methyluracil is prepared from 5-methyluracil, hexamethyldisiloxane trimethylchlorosilane HCl and 2,3 dihydrofuran. Chloroform is used as the organic chlorinated aliphatic hydrocarbons solvent and the process temperature is from 0° to +5° C. The end product is recrystallized from water. The yield of the final product is 70 percent of theory, calculating with reference to the starting 5-methyluracil. The m.p. 183°-185° C.

Found, in percent by weight: C 55.10 H 6.25 N 14.40 Calculated, in percent by weight: C 55.09 H 6.16 N 14.28 $C_9H_{12}O_3N_2$.

We claim:

1. A method for preparing $N_1$-(2'-furanidyl)-5-substituted uracils having the general formula

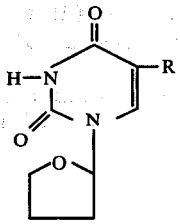

where R is selected from the group consisting of hydrogen, halogens, and methyl which comprises the steps of reacting a 2,4-bis(trimethylsilyloxy)-5 R-substituted pyrimidine where R is as above, with a solution of 2,3-dihydrofuran in an organic chlorinated lower aliphatic hydrocarbon solvent which solution is being saturated with anhydrous hydrogen chloride, said reaction being conducted at a temperature below about 10° C, and the reaction product is then isolated by precipitation with an alkanol.

2. The method according to claim 1, wherein said solvent is selected from the group consisting of dichloroethane, chloroform, and dichloromethane.

3. The method according to claim 1, wherein the process is carried out at a temperature from −5° to +5° C.

* * * * *